United States Patent [19]
Yoo et al.

[11] Patent Number: 5,952,504
[45] Date of Patent: Sep. 14, 1999

[54] 4-AMINO-3-ACYLNAPHTHYRIDINE DERIVATIVES

[75] Inventors: Han Yong Yoo; Kae Jong Chung; Man Sik Chang, all of Seoul; Sung Gyu Kim, Taejeon; Wahn Soo Choi, Seoul; Dae Pil Kang; Young Hun Kim, both of Pyungtack; Jang Hoon Paek, Seoul; Sang Kwon Sohn; Bog Goo Kang, both of Suwon; Young Heui Kim, Pyungtack; Kwi Hyon Seo, Suwon, all of Rep. of Korea

[73] Assignee: Yungjin Pharmaceutical Company, Ltd., Seoul, Rep. of Korea

[21] Appl. No.: 08/849,740

[22] PCT Filed: Jun. 1, 1996

[86] PCT No.: PCT/KR96/00080

§ 371 Date: Jul. 3, 1997

§ 102(e) Date: Jul. 3, 1997

[87] PCT Pub. No.: WO97/03074

PCT Pub. Date: Jan. 30, 1997

[30] Foreign Application Priority Data

Jul. 12, 1995 [KR] Rep. of Korea .................. 95-20514

[51] Int. Cl.$^6$ ............................................. C07D 471/04
[52] U.S. Cl. ........................................... 546/122; 546/123
[58] Field of Search ..................................... 546/122, 123

[56] References Cited

U.S. PATENT DOCUMENTS 4,343,804  8/1982  Munsen, Jr. et al. .................. 424/258

FOREIGN PATENT DOCUMENTS

| | | |
|---|---|---|
| 0 115 469 | 8/1984 | European Pat. Off. |
| 0 339 768 | 2/1989 | European Pat. Off. |
| 0 334 491 | 9/1989 | European Pat. Off. |
| 0 346 208 | 12/1989 | European Pat. Off. |

OTHER PUBLICATIONS

Saccomani et al., Biochimica et Biophysica Acta, 1977, 465, 311–330.

Fiske et al., "The Colorimetric Determination of Phosphorus", The Journal of Biological Chemistry, 1925, 66, 375–440.

Brezin et al., "Survival Following Massive Resection of Small and Large Bowel; Water, Electrolyte and Blood Volume Studies", Gastroenterology, 1954, 26, 895–905.

Chien et al., "Synthesis and Antimalarial Evaluation of Some 1,7–Naphthyridines and 2,9–Diazaanthracenes", J. Med. Chem., 1968, 11(1), 164–167.

*Primary Examiner*—Bernard Dentz
*Attorney, Agent, or Firm*—Foley & Lardner

[57] ABSTRACT

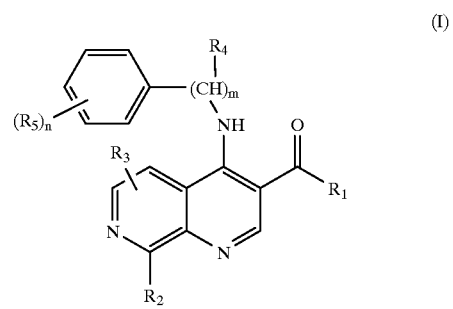

Novel 4-amino-3-acylnaphthyridine derivatives represented by formula (I), wherein $R_1$ is hydrogen, $C_1$–$C_6$ lower alkyl group, $C_1$–$C_6$ lower alkoxy group, $C_1$–$C_6$ lower alkoxyalkyl group, $C_3$–$C_6$ cycloalkyl group, $C_3$–$C_6$ cycloalkyl $C_1$–$C_6$ alkyl group, a or phenyl group which maybe substituted with $C_1$–$C_6$ alkyl group; $R_2$ is hydrogen, $C_1$–$C_6$ lower alkyl group, $C_1$–$C_6$ alkoxy group, $C_1$–$C_6$ alkylthio group, or a group of the formula: $NR_6R_7$ wherein $R_6$ and $R_7$, identical to or different from each other, are independently hydrogen or $C_1$–$C_6$ lower alkyl group, or $R_6$ and $R_7$ may form together 5-membered or 6-membered cycloalkyl group; $R_3$ is hydrogen, $C_1$–$C_6$ lower alkyl group, $C_1$–$C_6$ alkoxy group, $C_1$–$C_6$ alkylthio group, an amino group substituted with one or two $C_1$–$C_6$ alkyl groups, halogen, cyano group, $C_1$–$C_6$ alkanoyl group, or trifluoromethyl group; $R_4$ is hydrogen or a substituted or unsubstituted $C_1$–$C_6$ alkyl group; $R_5$ is hydrogen atom, $C_1$–$C_6$ lower alkyl group, $C_1$–$C_6$ alkoxy group, amino group substituted with one or two $C_1$–$C_6$ alkyl groups, $C_1$–$C_6$ alkylthio group, halogen, cyano group, hydroxycarbamoyl group, carboxy group, a $C_1$–$C_6$ alkanoyl group, or trifluoromethyl group, or alkyl group which forms together with $R_4$ a 5-membered or 6-membered cycloalkyl group; m is an integer from 0 to 4, inclusive; and n is an integer from 1 to 3 inclusive; with the proviso that all alkyl and alkoxy groups may be linear or branched, and said halogen means fluorine, chlorine or bromine atom, or a pharmaceutically acceptable salt therefore. These compounds show excellent anti-ulcer activity.

8 Claims, No Drawings

4-AMINO-3-ACYLNAPHTHYRIDINE DERIVATIVES

FIELD OF THE INVENTION

The present invention is related to new 4-amino-3-acylnaphthyridine derivatives or their pharmaceutically acceptable salts, which are useful as anti-ulcer or gastric juice-secretion suppressor, to a method for producing them and intermediates for the method.

BACKGROUND OF THE INVENTION

It has been reported that the gastrointestinal ulcers may be caused by an excessive secretion of acids such as hydrochloric acid or pepsin as well as by an action of anti-inflammatory agents such as indomethacin, toxic chemicals, pathogenic virus or toxic microorganisms. In particular, it had been reported that $H^+/K^+$ ATPase, a proton carrying enzyme which occurs in gastric mucosa, is involved in the formation of ulcer caused by a secretion of excess gastric juices.

EP 339768A, EP 0334491A and U.S. Pat. No. 4,343,804 disclose 4-aminoquinoline derivatives having an effective anti-gastric juice secretion activity.

The present inventors surprisingly found out that if quinoline nucleus of 4-aminoquinoline derivatives of the prior arts is replaced with naphthyridine parent-nucleus, the resulting new compounds showed potent anti-ulcer, anti-gastric juice secretion and anti-$H^+/K^+$ ATPase activities.

SUMMARY OF THE INVENTION

Therefore, an object of the present invention is to provide new 4-amino-3-acylnaphthyridine derivatives represented by the following general formula (I):

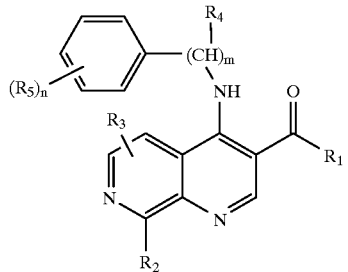

(I)

wherein $R_1$ is hydrogen atom, a $C_1$–$C_6$ lower alkyl group, a $C_1$–$C_6$ lower alkoxy group, $C_1$–$C_6$ lower alkoxyalkyl group, a $C_3$–$C_6$ cycloalkyl group, a $C_3$–$C_6$ cycloalkyl $C_1$–$C_6$ alkyl group, a substituted or unsubstituted phenyl, or a phenyl $C_1$–$C_6$ alkyl group of which phenyl group may be substituted;

$R_2$ is hydrogen atom, a $C_1$–$C_6$ lower alkyl group, a $C_1$–$C_6$ alkoxy group, a $C_1$–$C_6$ alkylthio group, or a group of a formula: $NR_6R_7$ wherein $R_6$ and $R_7$, identical to or different from each other, are independently hydrogen atom or a $C_1$–$C_6$ lower alkyl group, or $R_6$ and $R_7$ may form together 5-membered or 6-membered cycloalkyl group;

$R_3$ is hydrogen atom, a $C_1$–$C_6$ lower alkyl group, a $C_1$–$C_6$ alkoxy group, a $C_1$–$C_6$ alkylthio group, an amino group substituted with one or two $C_1$–$C_6$ alkyl groups, a halogen atom, a cyano group, a $C_1$–$C_6$ alkanoyl group, or trifluoromethyl group;

$R_4$ is hydrogen atom or a substituted or unsubstituted $C_1$–$C_6$ alkyl group;

$R_5$ is hydrogen atom, a $C_1$–$C_6$ lower alkyl group, a $C_1$–$C_6$ alkoxy group, an amino group substituted with one or two $C_1$–$C_6$ alkyl groups, a $C_1$–$C_6$ alkylthio group, a halogen atom, a cyano group, a hydroxycarbamoyl group, a carboxy group, a $C_1$–$C_6$ alkanoyl group, or trifluoromethyl group, or an alkyl group which forms together with $R_4$ a 5-membered or 6-membered cycloalkyl group;

m is an integer from 0 to 4, inclusive; and n is an integer from 1 to 3, inclusive;

with proviso that all alkyl and alkoxy groups may be linear or branched, and said halogen atom means fluorine, chlorine or bromine atom, or their pharmaceutically acceptable salts.

For the present invention, if a carbon atom to which $R_4$ other than hydrogen atom is bonded is asymmetric, the compounds (I) may have optically active isomers such as enantiomers, racemic mixtures, or mixtures thereof, all of them are embraced within scope of the present invention.

According to the present invention, a method for producing the compounds is also provided.

The above and other objects and features of the present invention will be apparent to the skilled in the art from the following detailed description.

DETAILED DESCRIPTION OF THE INVENTION

The pharmaceutically acceptable salts of the compound (I) of the present invention include acid-addition salts of the compound (I) with pharmaceutically acceptable organic and inorganic acids, for example hydrochloric, sulfuric, phosphoric, citric, formic, acetic, fumaric, maleic, malonic, tartaric, methanesulfonic, or p-toluene sulfonic acid.

The compound represented by the general formula (I) may be prepared by reacting the compound represented by the general formula (II)

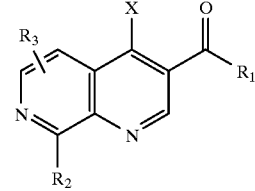

(II)

wherein, $R_1$, $R_2$, and $R_3$ have the same meanings as defined above; and X is a leaving group which may be substituted with an amine group, and may be exemplified by a halogen atom, $OS(O)_2R_8$ or $OP(O)(OR_9)_2$ in which $R_8$ is methyl, ethyl, trifluoromethyl, phenyl, or p-toluenyl group, and $R_9$ is methyl, ethyl, propyl, or phenyl group which may be substituted, with the compound represented by the general formula (III):

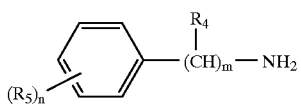

(III)

wherein, $R_4$, $R_6$, m and n have the same meanings as defined above.

The reaction of the compound (II) with the compound (III) can be carried out in a solvent, for example, not limited thereto, dichloromethane, chloroform, tetrahydrofuran, dioxan, anisole, acetonitrile, propionitrile, or dimethylformamide, dimethylsulfoxide at the temperature in the range of room temperature to boiling point of the solvent employed. The compound (III) may be used in an amount of equivalent to the compound (II) or more. A base may be added to facilitate the reaction. The base, which may be employed for this purpose, may include, not limited thereto, an inorganic base such as sodium carbonate, potassium carbonate, or sodium bicarbonate, or an organic base such as triethylamine, diisopropylethylamine, dimethylaniline, pyridine, or quinoline. If no base is added to the reaction system, the compound (III) is preferably used in an amount of more than 2 equivalents.

The compound (II) of the present invention can be prepared by following the reactions shown in the following Reaction Scheme 1.

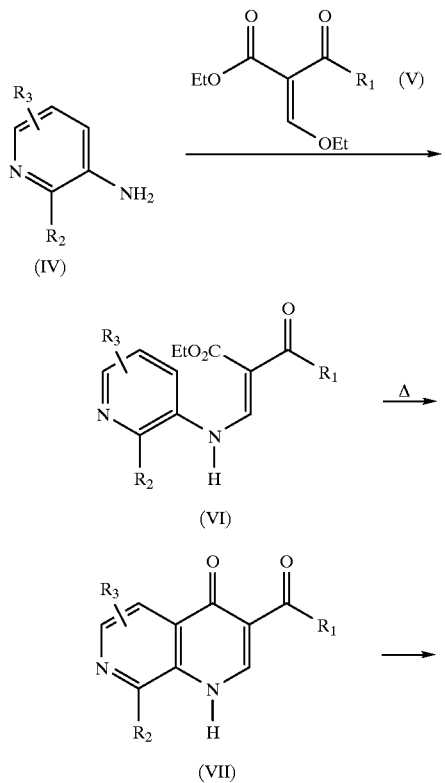

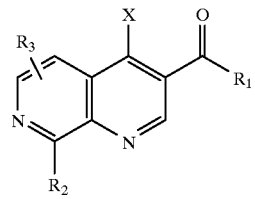

(II)

wherein, $R_1$, $R_2$, $R_3$, and X have the same meanings as defined above.

The compound (IV) is reacted with the compound (V) in absence of solvent at a temperature of 100° C. to 150°0 C., or in the presence of solvent selected from toluene, chlorobenzene or xylene at a temperature of the boiling point of the solvent employed to give the compound (VI). The compound (VI) is then subjected to cyclization in diphenyl ether by heating to a temperature of 200° C. to the boiling point of the solvent employed to prepare the naththylidine nucleus of the formula (VII). The compound (II) in which the group X is a halogen atom, preferably chlorine, can be prepared by reacting the compound (VII) with phosphoryl chloride, phosphorous trichloride, or phosphorous pentachloride under the reaction conditions known to those of skill in the art. The compound (II) in which the group X is sulfonate or phosphonate group can be prepared by reacting the compound (VII) with sulfonyl chloride or phosphoryl chloride in dichloromethane, chloroform, or 1,2-dichloroethane in the presence of a base such as triethylamine, diisopropylethylamine, dimethylaniline, pyridine or quinoline at a temperature of −10° C. to room temperature to give the compound (II).

The novel 4-amino-3-acylnaphthyridine derivatives represented by the general formula (I) or their pharmaceutically acceptable salts effectively inhibit $H^+/K^+$ ATPase, a proton carrying enzyme, so that they can be advantageously used for inhibiting the secretion of gastric juices or treating gastrointestinal ulcers.

The methods and results of pharmacological experiments and acute toxicity experiments carried out using the representative compounds (I) of the present invention are described below.

1. Inhibition of $H^+/K^+$ ATPase

Inhibition of $H^+/K^+$ ATPase, a proton carrying enzyme, was measured by following the procedure of Saccomani et al. [Biochim. Biophy. Acta., 465, 311–330 (1977)]. Thus, a homogenate of the gastric mucose membrane of rabbit was used to prepare vesicles containing $H^+/K^+$ ATPase by employing differential centrifugation and discontinuous density gradient centrifugation in Ficoll. The vesicles containing the enzyme were preincubated in a solution (0.5 ml) containing $1 \times 10^{-4}$M, $1 \times 10^{-5}$M, $1 \times 10^{-6}$M, or $1 \times 10^{-7}$M of the inventive compounds shown in Table 1 and 5 mM of imidazole buffer (pH 7.4) at a temperature of about 37° C. for about 30 minutes. Omeprazole was used as a control. A solution containing 2 mM of magnesium chloride, 40 mM of imidazole buffer (pH 7.4), 10 mM of potassium chloride and 10 m of ATP was added to the mixture. The resulting mixture was incubated at 37° C. for 15 minutes and the reaction was terminated by adding 1 ml of ice-cold 22% solution of trichloroacetic acid. Enzyme activity was calculated by measuring the separated inorganic phosphate by following the method of Fiske and Subbarow [J. Biol. Chem., 66, 375–440 (1925)]. The concentrations ($IC_{50}$) of the test compounds which inhibit the enzyme activity by 50% are shown in Table 1.

TABLE 1

| Test Compound | $H^+/K^+$ ATPase Inhibition ($IC_{50}$, $10^{-5}$ M) |
| --- | --- |
| Example 11 | 3.16 |
| Example 13 | 2.51 |
| Example 21 | 4.57 |
| Example 29 | 2.69 |
| Example 31 | 1.49 |
| Example 32 | 7.50 |
| Example 34 | 2.34 |
| Example 35 | 2.05 |
| Example 37 | 2.80 |
| Example 41 | 1.26 |
| Example 42 | 1.47 |
| Example 43 | 1.82 |
| Example 44 | 1.14 |
| Example 45 | 3.93 |
| Example 55 | 1.68 |
| Omeprazole | $5.75 \times 10^{-5}$ M |

2. Inhibition of Gastric Secretion

Inhibition of gastric secretion was measured by following the procedure of Shay ligation (Gastroenterology, 1954, 26, 903). Thus, male Sprague-Dawley rats weighing 180–200 g were starved for 24 hours and their pylorus were ligated. Then, the inventive compounds shown in Table 2 or omeprazole as a positive control was administered into duodenum. Four hours later, the stomach was removed, and the acidity and amount of gastric juice were measured. By comparing the measured values with the acidity and amount of the gastric juice of the stomach of the reference group to which no test compound was administered, the inhibition of gastric secretion was calculated. The effective dose ($ED_{50}$) of the test compounds which inhibit the gastric secretion by 50% are shown in Table 2.

TABLE 2

| Test Compound | Gastric juice Secretion Inhibition ($ED_{50}$, mg/kg) |
| --- | --- |
| Example 13 | 42.1% (12.5 mg/kg) |
| Example 15 | 30.0 |
| Example 21 | 11.7 |
| Example 32 | 36 6 |
| Example 34 | 30.0 |
| Example 37 | 13.3 |
| Example 49 | 35.8% (12.5 mg/kg) |

3. Ulcer Inhibition

1) Inhibition of ethanol-induced lesions

Inhibitory activity of the inventive compound on the ethanol-induced lesions was measured by using male Sprague-Dawley rats weighing 180–200 g. Thus, rats were starved for 24 hours, and the inventive compounds shown in Table 3 or omeprazole as a positive control was orally administered. Thirty minutes later, absolute ethanol (5 ml/kg) was orally administered. 1.5 hours later, the stomach was removed, and the degree of the wound of the stomach was measured. By comparing the measured values with the degree of the wound of the stomach of the reference group to which no test compound was administered, the concentrations ($IC_{50}$) of the test compounds which inhibit the ulcer by 50% were calculated and are shown in Table 3.

2) Inhibition of mepirizole-induced ulcer

Inhibitory activity of the inventive compound on the mepirizole-induced ulcer was measured by using male Spraque-Dawley rats weighing 200–230 g. Thus, rats were not starved, and the inventive compounds shown in Table 3 or omeprazole as a positive control was orally administered. Thirty minutes later, mepirizole suspended in 1% CMC (250 mg/kg) was orally administered. Before administration, the rats were starved for 24 hours, the duodena were removed. The degree of the ulcer thereof was measured. By comparing the measured values with the degree of the ulcer of the duodena of the reference group to which no test compound was administered, the effective doses ($ED_{50}$) of the test compounds which inhibit the ulcer by 50% were calculated and are shown in Table 3.

3) Inhibition of indomethacin-induced lesions

Inhibitory activities of the inventive compounds on the indomethacin-induced lesions were measured by using male Sprague-Dawley rats. Thus, rats were starved for 48 hours and prohibited from being supplied with water for 2 hours, and 35 mg/kg of indomethacin (Sigma Co.) as a causative of gastric lesions was subcutaneously administered. Before indomethacin treatment, the inventive compounds shown in Table 3 or omeprazole as a positive control was orally administered, and the inhibitions of lesions by the action of the test compounds were observed. The effective doses ($ED_{50}$) of the test compounds which inhibit the lesions by 50% were measured and are shown in Table 3.

4) Inhibition of stress-induced ulcer

Inhibitory activity of the inventive compound on the stress-induced ulcer was evaluated by using male Spraque-Dawley rats. Thus, rats were starved for 24 hours prior to carrying out the experiment.

Stress is an important factor for causing gastric ulcer, and was applied to rats by immersing them in water. Then, the inventive compounds shown in Table 3 or omeprazole as a control was orally administered, and the inhibitions of ulcer by the action of the test compounds were observed. The concentrations ($ED_{50}$) of the test compounds which inhibit the ulcer by 50% were measured and are shown in Table 3.

5) Inhibition of acetic acid-induced ulcer

Inhibitory activity of the inventive compound on the acetic acid-induced ulcer was evaluated by using male Sprague-Dawley rats. Thus, rats were starved for 5 hours prior to carrying out the experiment.

20 Microliter of 30% acetic acid was injected into the submucosal layer of the stomach using a microsyringe to induce a circular ulcer on the stomach. Various doses of the inventive compounds or omeprazole as a positive control were orally administered for 10 days, and the healing of ulcer by the action of the test compounds were observed. The percentages of the healing of the ulcer were calculated by comparing them with that of reference group.

TABLE 3

| Test Compound | Anti-ulcer activity ($ED_{50}$, mg/kg) | | | | |
| --- | --- | --- | --- | --- | --- |
| | Ethanol | Mepirizole | Indomethacin | Stress | Acetic acid* |
| Control (Omeprazole) | 17.5 | 2.8 | 1.2 | 4.4 | 27.1 |
| Ex. 21 | 11.2 | 64.1 | 2.1 | 13.0 | 22.0 |
| Ex. 15 | 12.8 | — | 2.1 | — | — |
| Ex. 34 | 30.6 | — | 4.9 | — | — |

*Percentage of healing in 30 mg/kg

4. Acute Toxicity

ICR mice (male and female) were orally administered with high doses (maximum dose: 5 g/kg) of inventive compound (Example 21) and were observed for their sudden death or a lasting of morbid conditions for 14 days. A median lethal dose ($LD_{50}$) an index of acute toxicity was measured and is Table 4

TABLE 4

| Compound | Sexuality | Dose (mg/kg) | No. of animals | No. of Death | Lethality (%) | $LD_{50}$ (mg/kg) |
|---|---|---|---|---|---|---|
| Ex. 21 | Male | 0 | 6 | 0 | 0 | 2336 |
| | | 40 | 6 | 0 | 0 | |
| | | 200 | 6 | 0 | 0 | |
| | | 1000 | 6 | 0 | 0 | |
| | | 5000 | 6 | 6 | 100 | |
| | Female | 0 | 6 | 0 | 0 | 1133 |
| | | 40 | 6 | 0 | 0 | |
| | | 200 | 6 | 0 | 0 | |
| | | 1000 | 6 | 1 | 17 | |
| | | 5000 | 6 | 6 | 100 | |

As can be seen from the results of Tables 1 to 4, it was confirmed that 4-amino-3-acylnaphthyridine derivatives show excellent inhibitory activity against $H^+/K^+$ ATPase and effectively suppress the secretion of gastric juices so that they can advantageously be used as an anti-ulcer agent.

The present invention will be described in more detail by way of Examples.

EXAMPLE 1

Preparation of ethyl 4-(2-methylphenylamino)-8-methoxy-1,7-naphthyridine-3-carboxylate (A) Ethyl 2-ethoxycarbonyl-3-(2-methoxypyridine-3-yl) aminoacrylate 3-amino-2-methoxypyridine (12.0 g) was reacted with diethyl ethoxymethylene malonate (23.0 g) at a temperature of 120° C. to 130° C. for 30 minutes while distilling ethanol produced during the reaction. After completion of the reaction, the reaction mixture was cooled to 60° C., and poured into petroleum ether (200 ml) and cooled to 0° C. The resulting precipitates were filtered to give 23.5 g (82%) of the titled compound.

m.p.: 65° C.
$^1$H-NMR (CDCl$_3$): δ1.35(t, 3H), 1.40(t, 3H), 4.19(s, 3H), 4.27(g, 2H), 4.32(g, 2H), 6.95(dd, 1H), 7.49 (d, 1H), 7.94 (d, 1H), 8.51(d, 1H).

(B) Ethyl 8-methoxy-1,7-naphthyridin-4(1H)-one-3-carboxylate 28.5 g of ethyl 2-ethoxycarbonyl-3-(2-methoxypyridin-3-yl)aminoacrylate prepared in the above (A) was dissolved in 150 ml of diphenyl ether, and the resulting solution was heated to reflux for 1.5 hours and cooled to about 60° C. Petroleum ether was added to give precipitates, which were filtered to give 14.1 g (59%) of the titled compound as brown crystals.

m.p.: 230–233° C.
$^1$H-NMR (CDCl$_3$/DMSO-d$_6$): δ 1.40(t, 3H), 4.18(s, 3H), 4.37(g, 2H), 7.69(d, 1H), 8.03(d, 1H), 8.51(s, 1H), 12.05 (br.s, 1H).

C) Ethyl 4-methanesulfonyloxy-8-methoxy-1,7-naphthyridin-3-carboxylate 4.96 g of ethyl 8-methoxy-1,7-naphthyridin-4(1H)-one-3-carboxylate and 4.2 ml of triethylamine were dissolved into 70 ml of dichloromethane, and a solution of methanesulfonyl chloride (1.85 ml) in dichloromethane (10 ml) was added dropwise at a temperature of 0° C. to 5° C. The resulting mixture was stirred for 1 hour at the same temperature. Water was added, and the resulting mixture was extracted with dichloromethane three times, and the organic phase was washed with water and then brine, dried over magnesium sulfate and distilled under reduced pressure. Ether was added to the residue to give 4.4 g (67%) of the titled compound as yellow crystals.

$^1$H-NMR (CDCl$_3$): δ 1.48(t, 3H), 3.56(s, 3H), 4.25(s, 3H), 4.50(g, 2H), 7.71(d, 1H), 8.31(d, 1H), 9.40(s, 1H).

(D) Ethyl 4-(2-Methylphenylamino)-8-methoxy-1,7-naphthyridin-3-carboxylate

Ethyl 4-methanesulfonyloxy-8-methoxy-1,7-naphthyridin-3-carboxylate (261 mg and o-toluidine (0.17 nl) were dissolved into 7 ml of acetonitrile and the solution was heated to reflux for 30 minutes. After cooling the mixture, the solvent was evaporated under reduced pressure and the beside was dissolved into chloroform. The solution was washed with water and then saturated sodium bicarbonate, dried, and concentrate under reduced pressure. The residue was subjected to silica gel column chromatography using a mixture of hexane:ethyl acetate (2:1) as an eluant to give yellow titled compound (180 mg, 67%).

m.p. 158° C.
$^1$H-NMR (CDCl$_3$): δ 1.47(t, 3H), 2.39(s, 3H), 4.19(s, 3H), 4.48(g, 2H), 6.69(d, 1H), 6.89–7.37(m, 4H), 7.68(d, 1H), 9.29(s, 1H), 10.47(br.s, 1H).

EXAMPLES 2–17

By following the procedure described in Example 1(D) by employing ethyl 4-methanesulfonyloxy-8-methoxy-1,7-naphthyridin-3-carboxylate prepared in Example 1(C) and various amines under, there were obtained inventive compounds of Examples 2–17. These compounds and their physical properties are shown in Table 5.

EXAMPLE 18

Preparation of 3-butyryl-4-(2-methylphenylamino)-8-methoxy-1,7-naphthyridine (A) Ethyl 2-butyryl-3-(2-methoxypyridine-3-yl) aminoacrylate 2-methoxy-3-aminopyridine (5.25 g) and ethyl 2-butyryl-3-ethoxy acrylate (9.44 g) were reacted at a temperature of 120° C. to 130° C. under heating for 30 minutes while distilling ethanol produced during the reaction. After completion of the reaction, the reaction mixture was cooled to 60° C., and poured into petrolium ether (100 ml) and cooled to 0° C. The resulting precipitates were filtered to give 11.24 g (90%) of the titled compound.

$^1$H-NMR (CDCl$_3$): δ 0.99(t, 3H), 1.38(t, 3H), 1.85(m, 2H), 2.97(t, 2H), 4.12(s, 3H), 4.30(g, 2H), 6.97(dd, 1H), 7.55(d, 1H), 7.99(d, 1H), 8.51(d, 1H), 12.68(br.s, 1H).

(B) 3-Butyryl-8-methoxy-1,7-naphthyridin-4(1H)-one 11.23 g of ethyl 2-butyryl-3-(2-methoxypyridine-3-yl) aminoacrylate prepared in the above (A) was dissolved in 60 ml so diphenyl ether, and the resulting solution was heated to reflux for 2 hours and cooled to about 50° C. Petroleum ether (200 ml) was added to give precipitates, which were filtered to give 6.3 g (76%) of the titled compound as brown crystals.

m.p.: 206–207° C.
$^1$H-NMR (CDCl$_3$/DMSO-d$_6$): δ 0.98(t, 3H), 1.69(m, 2H), 3.17(t, 2H), 4.15(s, 3H), 7.69(d, 1H), 8.04(d, 1H), 8.45(s, 1H), 12.23(br.s, 1H)

(C) 3-Butyryl-4-methanesulfonyloxy-8-methoxy-1,7-naphthyridine 4.93 g of 3-butyryl 8-methoxy-1,7-naphthyridin-4(1H)-one and 4.2 ml of triethylamine were dissolved into 70 ml of dichloromethane, and a solution of methanesulfonyl chloride (1.85 ml) in dichloromethane (10 ml) was added dropwise at a temperature of 0° C. to 5° C. The resulting mixture was stirred for 1 hour at the same temperature. Water was added, and the resulting mixture was extracted with dichloromethan three times, and the organic phase was washed with water and then brine, dried over magnesium sulfate and distilled under reduced pressure. Ether was added to the residue to give 4.61 g (71%) of the titled compound as yellow crystals.

m.p.: 184–185° C.

$^1$H-NMR (CDCl$_3$): δ 1.05(t, 3H), 1.81(m, 2H), 3.05(t, 2H), 3.49(s, 3H), 4.28(s, 2H), 7.67(s, 3H), 8.25(d, 1H), 9.17(s, 1H).

(D) 3-Butyryl-4-(2-methylphenylamino)-8-methoxy-1,7-naphthyridine

3-Butyryl-4-methanesulfonyloxy-8-methoxy-1,7-naphthyridine (259 mg) and o-toluidine (0.17 ml) were dissolved into 7 ml of acetonitrile, and the solution was extracted with chloroform, and the organic phase was washed with water and then saturated sodium bicarbonate. After drying, and concentration under reduced pressure, the resulting residue was subjected to silica gel column chromatography using a mixture of hexane:ethyl acetate (1:1) as an eluant to give yellow titled compound (150 mg, 56%).

m.p. 144° C.

$^1$H-NMR (CDCl$_3$): δ 1.08(t, 3H), 1.85(m, 2H), 2.35(s, 3H), 3.15(t, 2H), 4.19(s, 3H), 6.67(d, 1H), 6.95–7.38(m, 4H), 7.65(d, 1H), 8.22(s, 1H), 11.85(br.s, 1H).

EXAMPLES 19–32

By following the procedure described in Example 18(D) by employing 3-butyryl-4-methanesulfonyloxy-8-methoxy-1,7-naphthyridine prepared in Example 18(C) and various amines under, there were obtained inventive compounds of Examples 19–32. These compounds and their physical properties are shown in Table 5.

EXAMPLE 33

Preparation of 3-butyryl-8-ethoxy-4-(2-methylphenylamino)-1,7-naphthyridine (A) 3-Butyryl-8-ethoxy-4-methanesulfonyloxy-1,7-naphthyridine Ethyl 2-butyryl-3-(2-ethoxypyridin-3-yl)aminoacrylate (93%) was prepared from 3-amino-2-ethoxypyridine and ethyl 2-butyryl-3-ethoxyacrylate by following the procedure similar to that of Example 18(A), and then the product was subjected to cyclization in a similar manner to that of Example 18(B) to give 3-butyryl-8-ethoxy-1,7-naphthyridin-4(1H)-one (86%), which is then subjected to methanesulfonylation in a similar manner to that of Example 18(C) to give 3-butyryl-8-ethoxy-4-methanesulfonyloxy-1,7-naphthyridine (67%).

m.p. 115–116° C.

$^1$H-NMR (CDCl$_3$): δ 1.04(t, 3H), 1.50(t, 3H), 1.80(m, 2H), 3.00(t, 2H), 3.41(s, 3H), 4.32(s, 3H), 7.62(d, 1H), 8.23(d, 1H), 9.25(s, 1H).

(B) 3-Butyryl-8-ethoxy-4-(2-methylphenylamino)-1,7-naphthyridine

3-Butyryl-8-ethoxy-4-methanesulfonyloxy-1,7-naphthyridine (338 mg) and o-toluidine (214 mg) were dissolved into 7 ml of acetonitrile, and the solution was heated to reflux for 30 minutes and concentrated to evaporate solvent under reduced pressure. Water was added to the residue, and the mixture was extracted with chloroform, and the organic phase was washed with water and then saturated sodium bicarbonate. After dying, and concentration under reduced pressure, the resulting residue was subjected to silica gel column chromatography using a mixture of hexane:ethyl acetate (2:1) as an eluant to give yellow titled compound (300 mg, 86%)

m.p. 112° C.

$^1$H-NMR (CDCl$_3$): δ 1.05(t, 3H), 1.55(t, 3H), 1.83(m, 2H), 2.36(s, 3H), 3.10(t, 2H), 4.61(g, 2H), 6.65(d, 1H), 6.91–7.38(m, 4H), 7.82(d, 1H), 9.25(d, 1H), 11.81(s, 1H).

EXAMPLES 34–42

By following the procedure described in Example 33(B) by employing 3-butyryl-8-ethoxy-4-(2-methylphenylamino)-1,7-naphthyridine prepared in Example 33(A) and various amines under, there were obtained inventive compounds of Examples 34–42. These compounds and their physical properties are shown in Table 5.

EXAMPLE 43

Preparation of 3-Butyryl-8-isopropoxy-4-(2-methylphenylamino)-1,7-naphthyridine (A) 3-Butyryl-8-isopropoxy-4-methanesulfonyloxy-1,7-naphthyridine 3-Amino-2-isopropoxypyridine was reacted in a similar manner to that of Example 33(A) to give the titled compound.

$^1$H-NMR (CDCl$_3$): δ 1.05(t, 3H), 1.51(d, 6H), 1.80(m, 2H), 3.02(t, 2H), 3.45(s, 3H), 5.69(s, 3H), 7.61(d, 1H), 8.23(d, 1H), 9.19(s, 1H).

(B) 3-Butyryl-8-isopropyl-4-(2-methylphenylamino)-1,7-naphthyridine

By following a similar procedure described in Example 33(B) using 3-Butyryl-8-isopropyl-4-methanesulfonyloxy-1,7-naphthyridine (282 mg) and o-toluidine (0.17 ml) to give the titled compound (168 mg, 58%).

$^1$H-NMR (CDCl$_3$): δ 1.03(t, 3H), 1.52(d, 6H), 1.82(s, 3H), 2.38(s, 3H), 3.10(q, 2H), 5.59(m, 1H), 6.62(d, 1H), 6.90–7.35(m, 4H), 7.85(d, 1H), 9.30(s, 1H), 11.80(s, 1H).

EXAMPLES 44–45

By following the procedure described in Example 43(B) by employing 3-butyryl-8-isopropoxy-4-methanesulfonyloxy-1,7-naphthyridine prepared in Example 43(A) and various amines, there were obtained inventive compounds of Examples 44–45. These compounds and their physical properties are shown in Table 5.

EXAMPLE 46

Preparation of Ethyl-4-(2-methylphenylamino)-8-(4-morpholino)-1,7-naphthyridin-3-carboxylate (A) Ethyl 4-methanesulfonyloxy-8-(4-morpholino)-1,7-naphthyridin-3-carboxylate 3-Amino-2-(4-morpholino)pyridine was reacted in similar manners to those of Example 1(A)–(C) to give the titled compound.

$^1$H-NMR (CDCl$_3$): δ 1.45(t, 3H), 3.51(s, 3H), 3.80–4.05 (m, 8H), 4.49(q, 2H), 7.50(d, 1H), 8.29(d, 1H), 9.27(s, 1H).

(B) Ethyl 4-(2-methylphenylamino)-8-(4-morpholino)-1,7-naphthyridin-3-carboxylate By following a similar procedure described in Example 1(D) using ethyl 4-methanesulfonyloxy-8-(4-morpholino)-

1,7-naphthyridin-3-carboxylate (305 mg) and o-toluidine (0.17 ml) to give the titled compound (203 mg, 65%).

$^1$H-NMR (CDCl$_3$): δ 1.46(t, 3H), 2.40(s, 3H), 3.75–4.01 (m, 8H), 4.45(q, 2H), 6.65(d, 1H), 6.80–7.35(m, 4H), 7.75 (d, 1H), 9.19(s, 1H).

EXAMPLES 47–57

By following the procedure described in Example 46(B) by employing ethyl 4-methanesulfonyloxy-8-(4-morpholino)-1,7-naphthyridin-3-carboxylate prepared in Example 46(A), there were obtained inventive compounds of Examples 47–57. These compounds and their physical properties are shown in Table 5.

EXAMPLE 58

Preparation of Ethyl 4-(2-methylphenylamino)-8-(1-piperidino)-1,7-naphthyridin-3-carboxylate Ethyl 4-methanesulfonyloxy-8-(1-piperidino)-1,7-naphthyridin-3-carboxylate (303 mg) prepared by reacting 3-amino-2-(1-piperidino)pyridine in same manners as those of Example 1(A)–(C) was reacted with o-toluidine (0.17 ml) in the same manner as that of Example 1(D) to give the titled compound (187 mg, 60%).

$^1$H-NMR (CDCl$_3$): δ 1.25(t, 3H), 1.60–1.90(m, 6H), 2.25(s, 3H), 3.81(m, 4H), 4.45(q, 2H), 6.59(d, 1H), 6.80–7.38(m, 4H), 7.78(d, 1H), 9.20(s, 1H), 10.25(br.s, 1H).

EXAMPLE 59

Preparation of Ethyl 4-(1-indanylamino)-8-(1-piperidino)-1,7-naphthyridin-3-carboxylate Ethyl 4-methanesulfonyloxy-8-(1-piperidino)-1,7-naphthyridin-3-carboxylate (303 mg) prepared in Example 58 was reacted with 1-aminoindane in the same manner as that of Example 58 to give the titled compound (60%).

$^1$H-NMR (CDCl$_3$): δ 1.39(t, 3H), 1.62–1.88(m, 6H), 2.00–2.23(m, 1H), 2.65–3.15(m 3H), 3.80(m, 4H), 4.45(q, 2H), 5.64(q, 1H), 7.20–7.50(m, 5H), 8.04(d, 1H), 9.05(d, 1H), 9.08(s, 1H).

TABLE 5

| Compound | R$_1$ | R$_2$ | Ar | Yield (%) | m.p. (°C.) | $^1$H-NMR(CDCl$_3$) |
| --- | --- | --- | --- | --- | --- | --- |
| Example 2 | Ethoxy | Methoxy | Phenyl | 62 | 127 | 1.45(t, 3H), 4.20(s, 3H), 4.48(q, 2H), 6.85(d, H), 7.05–7.40(m, 5H), 7.75(d, 1H), 9.30(s, H), 10.50(br.s, 1H). |
| Example 3 | Ethoxy | Methoxy | 2-Methoxyplenyl | 67 | 194 | 1.45(t, 3H), 3.84(s, 3H), 4.21(s, 3H), 4.48(q, 2H) 6.80–7.25(m, 5H), 6.78(d, 1H), 9.29(s, 1H), 10.39(s, 1H). |
| Example 4 | Ethoxy | Methoxy | 2-Trifluoromethyl phenyl | 35 | 146 | 1.44(t, 3H), 4.20(s, 3H), 4.50(q, 2H), 6.70(d, 1H), 6.82(d, 1H), 7.35(m, 3H), 7.79(d, 1H), 9.39(s, 1H), 10.55(s, 1H). |
| Example 5 | Ethoxy | Methoxy | 2-Chlorophenyl | 58 | 160 | 1.45(t, 3H), 4.21(s, 3H), 4.49(g, 2H), 6.82(d, 1H), 6.83(m, 1H), 7.15(m, 2H), 7.53(m, 1H), 7.80(d, 1H) 9.38(s, 1H), 0.39((s, 1H). |
| Example 6 | Ethoxy | Methoxy | 2-Fluorophenyl | 60 | 146 | 1.49(t, 3H), 4.22(s, 3H), 4.50(g, 2H), 6.88(d, 1H), 7.00–7.25(m, 4H), 7.79(d, 1H), 9.33(s, 1H), 10.39(s, 1H). |
| Example 7 | Ethoxy | Methoxy | 4-Methylphenyl | 61 | 151 | 1.45(t, 3H), 2.39(s, 3H), 4.20(s, 3H), 4.47(q, 2H), 6.85(d, 1H), 6.99(d, 2H), 7.18(d, 2H), 7.72(d, 1H), 9.28(s, 1H), 10.49(s, 1H). |
| Example 8 | Ethoxy | Methoxy | 3-Methoxyphenyl | 64 | 174 | 1.47(t, 3H), 3.78(s, 3H), 4.20(s, 3H), 4.49(q, 2H), 6.60–6.81(m, 3H), 6.95(d, 1H), 7.21 (d, 1H), 7.79(d, 1H), 9.29(s, 1H), 10.45(s, 1H). |
| Example 9 | Ethoxy | Methoxy | 4-Methoxyphenyl | 60 | 139 | 1.46(t, 3H), 3.85(s, 3H), 4.19(s, 3H), 4.45(q, 2H), 6.81(d, 1H), 6.90(d, 2H), 7.05(d, 2H), 7.70(d, 1H), 9.25(s, 1H), 10.55(s, 1H). |
| Example 10 | Ethoxy | Methoxy | 3-Fluorophenyl | 57 | 152 | 1.49(t, 3H), 4.22(s, 3H), 4.50(q, 2H), 6.72–6.98(m, 3H), 7.30(m 1H), 7.81(d, 1H), 9.35(s, 1H), 10.40(s, 1H). |
| Example 11 | Ethoxy | Methoxy | 4-Fluorophenyl | 59 | 161 | 1.47(t, 3H), 4.19(s, 3H), 4.48(q, 2H), 6.79(d, 1H), 7.05(d, 4H), 7.75(d, 1H), 9.30(s, 1H), 10.45(s, 1H). |
| Example 12 | Ethoxy | Methoxy | 4-n-Butoxyphenyl | 44 | 105 | 1.00(t, 3H), 1.50(t, 3H), 1.52(m, 2H), 1.78(m, 2H), 3.96((t, 2H), 4.19(s, 3H), 4.45(q, 2H), 6.81(d, 1H), 6.85(d, 2H), 7.05(d, 2H), 7.71(d, 1H), 9.25(s, 1H), 10.55(s, 1H). |
| Example 13 | Ethoxy | Methoxy | 4-n-Butylphenyl | 37 | 108 | 0.97(t, 3H), 1.25–1.70(m, 4H), 1.45(t, 3H), 2.63(t, 2H), 4.20(s, 3H), 4.47(q, 2H), 6.85(d, 1H), 7.00(d, 2H), 7.17(d, 2H), 7.71(d, 2H), 9.27(s, 1H), 10.48(s, 1H). |
| Example 14 | Ethoxy | Methoxy | (R)-1-Phenylethyl | 69 | 109 | 1.45(t, 3H), 1.69(d, 3H), 4.15(s, 1H), 4.44(q, 2H), 5.30(m, 1H), 7.35(m, 6H), 7.80(d, 1H), 9.18(s, 1H), 9.55(d, 1H). |
| Example 15 | Ethoxy | Methoxy | (S)-2-Phenylethyl | 60 | 110 | 1.45(t, 3H), 1.69(d, 3H), 4.14(s, 1H), 4.45(q, 2H), 5.30(m, 1H), 7.35(m, 6H), 7.80(d, 1H), 9.19(s, 1H), 9.55(d, 1H). |
| Example 16 | Ethoxy | Methoxy | Benzyl | 85 | 148 | 1.42(t, 3H), 4.20(s, 3H), 4.40(q, 2H), 5.00(d, 2H), 7.40(m, 5H), 7.55(d, 1H), 7.91(d, 1H), 9.19(s, 1H), 9.55(br.s, 1H). |
| Example 17 | Ethoxy | Methoxy | 2-Methylthiophenyl | 71 | 174 | 1.45(t, 3H), 2.53(s, 3H), 4.20(s, 3H), 4.45(q, 2H), 6.76(d, 1H), 6.77–7.40(m, 4H), 7.75(d, 1H), 9.19(s, 1H), 10.40(s, 1H). |
| Example 19 | n-Propyl | Methoxy | 4-Methylphenyl | 62 | 145 | 1.05(t, 3H), 1.82(m, 2H), 2.39(s, 3H), 3.13(t, 2H), 4.19((s, 3H), 6.83(d, 1H), 7.01(d, 2H), 7.18(d, 2H), 7.70(d, 1H), 9.21(s, 1H), 11.82(s, 1H). |
| Example 20 | n-Propyl | Methoxy | Phenyl | 64 | 119 | 1.05(t, 3H), 1./81(m, 2H), 3.12(t, 2H), 4.20(s, 3H), 6.82(d, 1H), 7.09–7.40(m, 5H), 7.71(d, 1H), 9.22(s, 1H), 11.81(s, 1H). |
| Example 21 | n-Propyl | Methoxy | (R)-1-Phenylethyl | 57 | 111 | 1.07(t, 3H), 1.73(d, 3H), 1.82(m, 2H), 3.08(t, 2H), 4.18(s, 3H), 5.37(m, 1H), 7.25–7.49(m, 6H), 7.80(d, 1H), 9.15(s, 1H), 11.31(d, 1H). |
| Example 22 | n-Propyl | Methoxy | (S)-1-Phenylethyl | 54 | 110 | 1.05(t, 3H), 1.73(d, 3H), 1.81(m, 2H), 3.08(t, 2H), 4.18(s, 3H), 5.38(m, 1H), 7.24–7.46(m, 6H), 7.79(d, 1H), 9.13(s, 1H), 11.13(d, 1H). |
| Example 23 | n-Propyl | Methoxy | 2-Methoxyphenyl | 63 | 135 | 1.03(t, 3H), 1.81(m, 2H), 3.12(t, 2H), 3.79(s, 3H), 4.20(s, 3H), 6.83–7.27(m, 5H), 7.70(d, 1H), 9.21(s, 1H), 11.67(s, 1H). |
| Example 24 | n-Propyl | Methoxy | 3-Methoxyphenyl | 60 | 144 | 1.07(t, 3H), 1.83(m, 2H), 3.18(t, 2H), 3.80(s, 3H), 4.20(s, 3H), 6.65–6.85(m, 4H), 6.95(d, 1H), 7.30(d, 1H), 7.78(d, 1H), 9.25(s, 1H), 11.80(s, 1H). |
| Example 25 | n-Propyl | Methoxy | 4-Methoxyphenyl | 50 | 125 | 1.05(t, 3H), 1.82(m, 2H), 3.16(t, 2H), 3.82(s, 3H), 4.19(s, 3H), 6.80(d, 1H), 6.91(d, 2H), 7.08(d, 2H), 7.69(d, 1H), 9.20(s, 1H), 11.90(s, 1H). |

TABLE 5-continued

| Compound | $R_1$ | $R_2$ | Ar | Yield (%) | m.p. (°C.) | $^1$H-NMR(CDCl$_3$) |
|---|---|---|---|---|---|---|
| Example 26 | n-Propyl | Methoxy | 2-Methylthiophenyl | 73 | 107 | 1.08(t, 3H), 1.85(m, 2H), 2.52(s, 3H), 3.15(t, 2H), 4.20(s, 3H), 6.75(d, 1H), 6.88–7.40(m, 4H), 7.71(d, 1H), 9.24(s, 1H), 11.76(s, 1H). |
| Example 27 | n-Propyl | Methoxy | Benzyl | 75 | 129 | 1.01(t, 3H), 1.79(m, 2H), 3.01(t, 2H), 4.19(m, 3H), 5.00(d, 2H), 7.40(m, 5H), 7.55(d, 1H), 7.90(d, 1H), 9.12(s, 1H), 11.05(br.s, 1H). |
| Example 28 | n-Propyl | Methoxy | 2-Phenylethyl | 64 | 98 | 1.03(t, 3H), 1.79(m, 2H), 3.05(m, 4H), 4.12(m, 2H), 4.20(s, 3H), 7.30(m, 5H), 7.60(d, 1H), 7.97(d, 1H), 9.05(s, 1H), 10.85(s, 1H). |
| Example 29 | n-Propyl | Methoxy | 4-Phenyl-n-butyl | 50 | 90 | 1.05(t, 3H), 1.80–2.05(m, 6H), 2.71(m, 2H), 3.03(t, 2H), 3.85(m, 2H), 4.21(s, 1H), 7.28(m, 5H), 7.60(d, 1H), 7.98(d, 1H), 9.05(s, 1H), 10.82(s, 1H). |
| Example 30 | n-Propyl | Methoxy | 4-n-Butylphenyl | 66 | 94 | 0.91(t, 3H), 1.04(t, 3H), 1.21–1.90(m, 6H), 2.62(t, 2H), 3.07(t, 2H), 4.18(s, 3H), 6.81(d, 1H), 7.02(d, 2H), 7.18(d, 2H), 7.65(d, 1H), 8.22(s, 1H), 11.80(s, 1H). |
| Example 31 | n-Propyl | Methoxy | 3-Indanyl | 34 | 156 | 1.05(t, 3H), 1.81(m, 2H), 2.15(m, 2H), 2.90(m, 4H), 3.12(t, 2H), 4.20(s, 3H), 6.85–7.03(m, 3H), 7.20(d, 1H), 7.70(d, 1H), 9.20(s, 1H), 11.86(s, 1H). |
| Example 32 | n-Propyl | Methoxy | 1,2,3,4-Tetrahydro 1-naphtyl | 31 | 119 | 1.02(t, 3H), 1.60–2.30(m, 6H), 2.87(m, 2H), 3.00(t, 2H), 4.20(s, 3H), 5.40(m, 1H), 7.10–7.35(m, 4H), 7.59(d, 1H), 7.99(d, 1H), 9.15(s, 1H), 10.75(d, 1H). |
| Example 34 | n-Propyl | Ethoxy | 2-Methylthiophenyl | 79 | 136 | 1.05(t, 3H), 1.58(t, 3H), 1.85(m, 2H), 2.52(s, 3H), 3.11(t, 2H), 4.62(q, 2H), 6.70(d, 1H), 6.85–7.38(m, 4H), 7.69(d, 1H), 9.25(s, 1H), 11.70(s, 1H). |
| Example 35 | n-Propyl | Ethoxy | 4-n-Butylphenyl | 86 | 121 | 0.96(t, 3H), 1.03(t, 3H), 1.25–1.90(m, 6H), 1.59(t, 3H), 2.61(t, 2H), 3.17(t, 2H), 4.61(q, 2H), 6.80(d, 1H), 7.01(d, 2H), 7.18(d, 2H), 7.65(d, 1H), 9.21(s, 1H), 11.80(s, 1H). |
| Example 36 | n-Propyl | Ethoxy | (S)-1-Phenylethyl | 69 | 75 | 1.03(t, 3H), 1.56(t, 3H), 1.70(d, 3H), 1.82(m, 2H), 3.05(t, 2H), 4.60(q, 2H), 5.35(m, 1H), 7.21–7.50(m, 6H), 7.78(d, 1H), 9.17(s, 1H), 11.07(d, 1H). |
| Example 37 | n-Propyl | Ethoxy | (R)-1-Phenylethyl | 69 | 76 | 1.03(t, 3H), 1.57(t, 3H), 1.69(d, 3H), 1.81(m, 2H), 3.05(t, 2H), 4.60(q, 2H), 5.36(m, 1H), 7.20–7.50(m, 6H), 7.78(d, 1H), 9.17(s, 1H), 10.05(d, 1H). |
| Example 38 | n-Propyl | Ethoxy | 4-Methylphenyl | 86 | 137 | 1.05(t, 3H), 1.58(t, 3H), 1.83(m, 2H), 2.39(s, 1H), 3.16(t, 2H), 4.62(q, 2H), 6.82(d, 1H), 6.96–7.23(q, 4H), 7.70(d, 1H), 9.25(s, 1H), 11.82(s, 1H). |
| Example 39 | n-Propyl | Ethoxy | 4-Fluorophenyl | 74 | 157 | 1.05(t, 3H), 1.57(t, 3H), 1.82(m, 2H), 3.12(t, 2H), 4.62(q, 2H), 6.75(d, 1H), 7.10(m, 4H), 7.70(d, 1H), 9.28(s, 1H), 11.79(s, 1H). |
| Example 40 | n-Propyl | Ethoxy | 2-Trifluoromethyl-phenyl | 57 | 160 | 1.06(t, 3H), 1.60(t, 3H), 1.89(m, 2H), 3.14(t, 2H), 4.68(q, 2H), 6.67(d, 1H), 6.90(d, 1H), 7.38(m, 2H), 7.73(d, 1H), 7.78(d, 1H), 9.32(s, 1H), 11.81(s, 1H). |
| Example 41 | n-Propyl | Ethoxy | 4-Phenyl-n-butyl | 57 | 73 | 1.01(t, 3H), 1.58(t, 3H), 1.58–1.90(m, 6H), 2.67(m, 2H), 3.00(t, 2H), 3.81(m, 2H), 4.62(q, 2H), 7.12–7.37(m, 5H), 7.58(d, 1H), 7.95(d, 1H), 9.08(s, 1H), 10.80(s, 1H). |
| Example 42 | n-Propyl | Ethoxy | 1,2,3,4-Tetrahydro 1-naphtyl | 59 | 136 | 1.02(t, 3H), 1.61(t, 3H), 1.68–2.30(m, 6H), 2.90(m, 2H), 3.00(t, 2H), 4.67(q, 2H), 5.42(m, 1H), 7.12–7.35(m, 4H), 7.60(d, 1H), 7.98(d, 1H), 9.18(s, 1H), 10.70(d, 1H). |
| Example 44 | n-Propyl | i-Propoxy | 2-Methylthiophenyl | 70 | 144 | 1.05(t, 3H), 1.52(d, 6H), 1.85(m, 2H), 2.51(s, 3H), 3.10(t, 2H), 5.60(m, 1H), 6.68(d, 1H), 6.82–7.40(m, 4H), 7.69(d, 1H), 9.30(s, 1H), 10.65(s, 1H). |
| Example 45 | n-Propyl | i-Propoxy | 2-Trifluoromethyl-phenyl | 36 | 127 | 1.04(t, 3H), 1.53(d, 6H), 1.84(m, 2H), 3.12(t, 2H), 5.61(m, 1H), 6.63(d, 1H), 6.92(d, 1H), 7.39(m, 2H), 7.73(d, 1H), 7.79(d, 1H), 9.37(s, 1H), 11.80(d, 1H). |
| Example 47 | Ethoxy | 4-Morpho-linyl | Phenyl | 73 | | 1.45(t, 1H), 3.95(m, 8H), 4.45(q, 2H), 6.80(d, 1H), 7.00–7.58(m, 5H), 7.80(d, 1H), 9.18(s, 1H), 10.40(s, 1H). |
| Example 48 | Ethoxy | 4-Morpho-linyl | 4-Methylphenyl | 68 | | 1.44(t, 3H), 2.38(s, 3H), 3.90(m, 8H), 4.45(q, 2H)6.81(d, 1H), 6.96(d, 2H), 7.15(d, 2H), 7.79(d, 1H), 9.19(s, 1H), 10.38(s, 1H). |
| Example 49 | Ethoxy | 4-Morpho-linyl | 2-Methoxyphenyl | 77 | | 1.43(t, 3H), 3.70–4.20(m, 1H), 4.42(q, 2H), 6.75–7.22(m, 5H), 7.81(d, 1H), 9.19(s, 1H), 10.21(s, 1H). |
| Example 50 | Ethoxy | 4-Morpho-linyl | 3-Methoxyphenyl | 72 | | 1.45(t, 3H), 3.78(s, 3H), 3.92(m, 8H), 4.45(q, 2H)6.60–7.30(m, 5H), 7.82(d, 1H), 9.20(s, 1H), 10.34(s, 1H). |
| Example 51 | Ethoxy | 4-Morpho-linyl | 4-Methyoxyphenyl | 69 | | 1.42(t, 3H), 3.75–4.03(m, 11H), 4.42(q, 2H), 6.71–7.10(m, 5H), 7.78(d, 1H), 9.17(s, 1H), 10.42(s, 1H). |
| Example 52 | Ethoxy | 4-Morpho-linyl | 2-Methylthiophenyl | 70 | | 1.46(t, 3H), 2.55(s, 3H), 3.91(m, 8H), 4.46(q, 2H), 6.67–7.40(m, 5H), 7.80(d, 1H), 9.20(s, 1H). |
| Example 53 | Ethoxy | 4-Morpho-linyl | 3-Methylthiophenyl | 63 | | 1.47(t, 3H), 2.45(s, 3H), 3.95(m, 8H), 4.45(q, 2H), 6.72–7.29(m, 5H), 7.83(d, 1H), 9.20(s, 1H), 10.18(s, 1H). |
| Example 54 | Ethoxy | 4-Morpho-linyl | 2-Fluorophenyl | 72 | | 1.47(t, 3H), 3.96(m, 8H), 4.45(q, 2H), 6.80(d, 1H), 6.90–7.20(m, 4H), 7.82(d, 1H), 9.20(s, 1H), 10.39(s, 1H). |
| Example 55 | Ethoxy | 4-Morpho-linyl | 3-Trifluoromethyl-phenyl | 70 | | 1.44(t, 3H), 3.97(br.s, 8H), 4.45(q, 2H), 6.71(d, 1H), 7.10–7.17(m, 4H), 7.85(d, 1H), 9.21(s, 1H), 10.22(s, 1H). |
| Example 56 | Ethoxy | 4-Morpho-linyl | 4-n-Butoxyphenyl | 67 | | 1.00(t, 3), 1.47(t, 3H), 1.42–1.85(m, 4H), 3.80–4.15(m, 8H), 4.44(q, 2H), 6.72–7.10(m, 5H), 7.79(d, 1H), 9.18(s, 1H), 10.40(s, 1H). |
| Example 57 | Ethoxy | 4-Morpho-linyl | 1-Indanyl | 65 | | 1.42(t, 3H), 2.15(m, 1H), 2.60–3.15(m, 3H), 3.80–4.15(m, 8H), 4.46(q, 2H), 5.65(q, 1H), 7.20–7.45(m, 4H), 7.57(d, 1H), 8.05(d, 1H), 9.10(s, 1H), 9.15(d, 1H). |

It is understood that the foregoing detailed description is given merely by way of illustration and that modifications and variations may be made therein without departing from the spirit and scope of the invention.

We claim:

1. A compound represented by the formula (I):

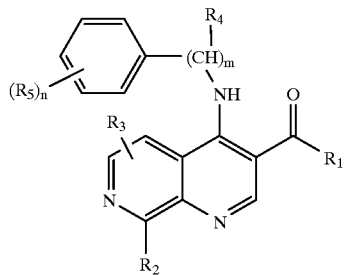

(I)

wherein
- $R_1$ is a hydrogen atom, a $C_1$–$C_6$ lower alkyl group, a $C_1$–$C_6$ lower alkoxy group, a $C_1$–$C_6$ lower alkoxyalkyl group, a $C_3$–$C_6$ cycloalkyl group, a $C_3$–$C_6$ cycloalkyl $C_1$–$C_6$ alkyl group, a substituted or unsubstituted phenyl group or a phenyl $C_1$–$C_6$ alkyl group of which the phenyl group may be substituted;
- $R_2$ is a hydrogen atom, a $C_1$–$C_6$ lower alkyl group, a $C_1$–$C_6$ alkoxy group, a $C_1$–$C_6$ alkylthio group, or a group of the formula: $NR_6R_7$ wherein $R_6$ and $R_7$, identical to or different from each other, are independently a hydrogen atom or a $C_1$–$C_6$ lower alkyl group, or wherein $R_6$ and $R_7$ may form together a 5-membered or 6-membered cycloalkyl group;
- $R_3$ is a hydrogen atom, a $C_1$–$C_6$ lower alkyl group, a $C_1$–$C_6$ alkoxy group, a $C_1$–$C_6$ alkylthio group, an amino group substituted with one or two $C_1$–$C_6$ alkyl groups, a halogen atom, a cyano group, a $C_1$–$C_6$ alkanoyl group, or a trifluoromethyl group;
- $R_4$ is a hydrogen atom or a substituted or unsubstituted $C_1$–$C_6$ alkyl group;
- $R_5$ is a hydrogen atom, a $C_1$–$C_6$ lower alkyl group, a $C_1$–$C_6$ alkoxy group, an amino group substituted with one or two $C_1$–$C_6$ alkyl groups, a $C_1$–$C_6$ alkylthio group, a halogen atom, a cyano group, a hydroxycarbamoyl group, a carboxy group, a $C_1$–$C_6$ alkanoyl group, or a trifluoromethyl group, or an alkyl group which forms together with $R_4$ a 5-membered or 6-membered cycloalkyl group;
- m is an integer from 0 to 4, inclusive; and
- n is an integer from 1 to 3, inclusive;
- with the proviso that all alkyl and alkoxy groups may be linear or branched, and said halogen atom is fluorine, chlorine or bromine;

or a pharmaceutically acceptable salt thereof.

2. The compound (I) according to claim 1, wherein $R_1$ is an ethoxy or propyl group; $R_2$ is a methoxy, ethoxy, propyl, isopropyl, hydroxyethoxy, piperidino or morpholino group; $R_3$ is a hydrogen atom; $R_4$ is a hydrogen atom, or methyl, or ethyl, $R_5$ is a hydrogen atom or a methyl, ethyl, vinyl, trifluoromethyl, methoxy, or ethoxy group, or chlorine or fluorine atom, or an allyl or butyl group, or an alkyl group forming together with $R_4$ a 5-membered or 6-membered cycloalkyl group; m is an integer of 0 to 4; and n is an integer of 1 or 2, or a pharmaceutically acceptable salt thereof.

3. The compound (I) according to claim 2, wherein $R_1$ is an ethoxy or propyl group; $R_2$ is a methoxy, ethoxy, or isopropyl group; $R_3$ is a hydrogen atom; $R_4$ is a methyl or ethyl group; $R_5$ is a hydrogen atom; m is an integer of 1; and n is an integer of 1, or a pharmaceutically acceptable salt thereof.

4. The compound (I) according to claim 2, wherein $R_1$ is an ethoxy or propyl group; $R_2$ is a methoxy, ethoxy, isopropyl, hydroxyethoxy, piperidino or morpholino group; $R_3$ is a hydrogen atom; $R_5$ is a hydrogen atom, or methyl, ethyl, vinyl, trifluoromethyl, methoxy, or ethoxy group, or chlorine or fluorine atom, or an allyl or butyl group, or an alkyl group forming together with $R_4$ a 5-membered or 6-membered cycloalkyl group; m is zero; and n is an integer of 1 or 2, or a pharmaceutically acceptable salt thereof.

5. The compound (I) according to claim 1, which is 3-Butyryl-4-(1,2,3,4-tetrahydro-1-naphthylamino)-8-methoxy-1,7-naphthyridine, or a pharmaceutically acceptable salt thereof.

6. The compound (I) according to claim 1, which is 3-Butyryl-4-(5-(R)-(+)-methylbenzylamino)-8-ethoxy-1,7-naphthyridine, or a pharmaceutically acceptable salt thereof.

7. A process for producing a compound represented by the formula (I):

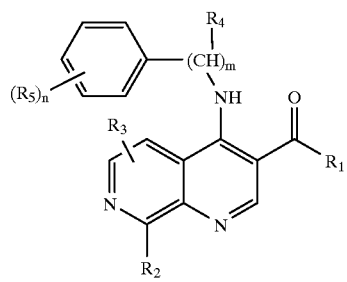

(I)

wherein
- $R_1$ is a hydrogen atom, a $C_1$–$C_6$ lower alkyl group, a $C_1$–$C_6$ lower alkoxy group, a $C_1$–$C_6$ lower alkoxyalkyl group, a $C_1$–$C_6$ cycloalkyl group, a $C_3$–$C_6$ cycloalkyl $C_1$–$C_6$ alkyl group, a substituted or unsubstituted phenyl group or a phenyl $C_1$–$C_6$ alkyl group of which the phenyl group may be substituted;
- $R_2$ is a hydrogen atom, a $C_1$–$C_6$ lower alkyl group, a $C_1$–$C_6$ alkoxy group, a $C_1$–$C_6$ alkylthio group, or a group of the formula: $NR_6R_7$ wherein $R_6$ and $R_7$, identical to or different from each other, are independently a hydrogen atom or a $C_1$–$C_6$ lower alkyl group, or wherein $R_6$ and $R_7$ may form together a 5-membered or 6-membered cycloalkyl group;
- $R_3$ is a hydrogen atom, a $C_1$–$C_6$ lower alkyl group, a $C_1$–$C_6$ alkoxy group, a $C_1$–$C_6$ alkylthio group, an amino group substituted with one or two $C_1$–$C_6$ alkyl groups, a halogen atom, a cyano group, a $C_1$–$C_6$ alkanoyl group, or a trifluoromethyl group;
- $R_4$ is a hydrogen atom or a substituted or unsubstituted $C_1$–$C_6$ alkyl group;
- $R_5$ is a hydrogen atom, a $C_1$–$C_6$ lower alkyl group, a $C_1$–$C_6$ alkoxy group, an amino group substituted with one or two $C_1$–$C_6$ alkyl groups, a $C_1$–$C_6$ alkylthio group, a halogen atom, a cyano group, a hydroxycarbamoyl group, a carboxy group, a $C_1$–$C_6$ alkanoyl group, or a trifluoromethyl group, or an alkyl group which forms together with $R_4$ a 5-membered or 6-membered cycloalkyl group;
- m is an integer from 0 to 4, inclusive; and
- n is an integer from 1 to 3, inclusive;
- with the proviso that all alkyl and alkoxy groups may be linear or branched, and said halogen atom is fluorine, chlorine or bromine, or a pharmaceutically acceptable salt thereof, which comprises the steps of reacting a compound represented by the formula (II):

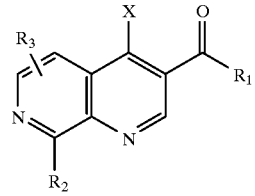
(II)

wherein,
$R_1$, $R_2$, and $R_3$ have the same meanings as defined above; and X is a chlorine atom, $OS(O)_2R_8$ or $OP(O)(OR_9)_2$ in which $R_8$ is a methyl, ethyl, trifluoromethyl, phenyl, or p-toluenyl group, and $R_9$ is a methyl, ethyl, propyl, or phenyl group which may be substituted, or a pharmaceutically acceptable salt thereof, with a compound represented by the formula (III)

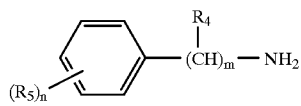
(III)

wherein
$R_4$, $R_5$, m and n have the same meaning as defined above.

8. The process according to claim 7, wherein the compound (II) or a pharmaceutically acceptable salt thereof are prepared by reacting a compound represented by the formula (IV):

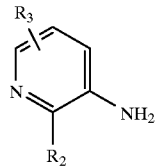
(IV)

wherein,
$R_2$ and $R_3$ have the same meanings as defined in claim 7, with a compound represented by the formula (V):

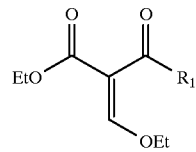
(V)

wherein,
$R_1$ has the same meaning as defined in claim 7, to give a compound represented by the formula (VI):

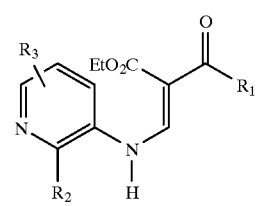
(VI)

wherein,
$R_1$, $R_2$, and $R_3$ have the same meanings as defined in claim 7; subjecting the compound (VI) to cyclization to give a compound represented by the formula (VII):

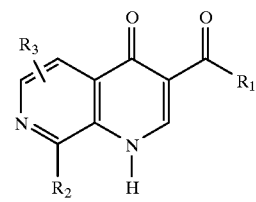
(VII)

wherein
$R_1$, $R_2$, and $R_3$ have the same meaning as defined in claim 7; subjecting the compound (VII) to halogenation, sulfonation or phosphonation to give the compound (II).

* * * * *